US009844714B2

(12) United States Patent
Greenwood

(10) Patent No.: US 9,844,714 B2
(45) Date of Patent: Dec. 19, 2017

(54) HORSE-RIDING TRAINING DEVICE

(71) Applicant: William Ronald Greenwood, Cheshire (GB)

(72) Inventor: William Ronald Greenwood, Cheshire (GB)

(*) Notice: Subject to any disclaimer, the term of this patent is extended or adjusted under 35 U.S.C. 154(b) by 0 days.

(21) Appl. No.: 14/658,106

(22) Filed: Mar. 13, 2015

(65) Prior Publication Data
US 2015/0258407 A1    Sep. 17, 2015

(30) Foreign Application Priority Data
Mar. 14, 2014  (GB) .................. 1404597.5

(51) Int. Cl.
*A63B 21/00* (2006.01)
*A63B 21/02* (2006.01)
*A63B 24/00* (2006.01)
*A63B 69/04* (2006.01)
*A63B 71/06* (2006.01)
*A63G 13/06* (2006.01)
*G06F 19/00* (2011.01)

(52) U.S. Cl.
CPC .......... *A63B 69/04* (2013.01); *A63B 24/0075* (2013.01); *A63G 13/06* (2013.01); *G06F 19/3481* (2013.01); *A63B 21/023* (2013.01); *A63B 21/4047* (2015.10); *A63B 71/0622* (2013.01); *A63B 2024/0081* (2013.01); *A63B 2071/063* (2013.01); *A63B 2071/0625* (2013.01); *A63B 2209/02* (2013.01); *A63B 2210/50* (2013.01); *A63B 2220/16* (2013.01); *A63B 2220/20* (2013.01); *A63B 2220/44* (2013.01); *A63B 2220/51* (2013.01); *A63B 2220/56* (2013.01); *A63B 2220/62* (2013.01); *A63B 2225/50* (2013.01)

(58) Field of Classification Search
CPC .................... A63B 69/04; A63B 21/02; A63B 21/04–21/0435; A63B 23/0211
See application file for complete search history.

(56) References Cited

U.S. PATENT DOCUMENTS 2,978,245 A * 4/1961 Rempel .................. A63G 13/08
                                                472/105
5,453,066 A * 9/1995 Richter, Jr. ............ A63B 69/04
                                                482/57
(Continued)

FOREIGN PATENT DOCUMENTS

DE   20 2005 019 790 U1    4/2006
GB         2 363 993 A     1/2002
(Continued)

OTHER PUBLICATIONS

Search Report for UK Patent Application No. 14 04597.5 dated Sep. 16, 2014.

*Primary Examiner* — Loan H Thanh
*Assistant Examiner* — Jennifer M Deichl
(74) *Attorney, Agent, or Firm* — Daniel A. Tanner, III

(57) ABSTRACT

A horse-riding training device comprises a base, a body portion for supporting a rider, the body portion being displaceably mounted on the base, a neck portion pivotally connected to the base and a resilient element which resists displacement of the body portion and the neck portion with respect to the base, which provides a realistic simulation of riding a horse.

27 Claims, 5 Drawing Sheets

(56) References Cited

U.S. PATENT DOCUMENTS

| | | | | |
|---|---|---|---|---|
| 7,998,039 B1* | 8/2011 | Wallach | ............... | A63B 21/023 |
| | | | | 482/121 |
| 2006/0147887 A1* | 7/2006 | Greenwood | ........... | A63B 69/04 |
| | | | | 434/247 |
| 2006/0217238 A1* | 9/2006 | Liao | ................. | A63B 23/03583 |
| | | | | 482/72 |
| 2011/0230314 A1* | 9/2011 | Hoffman | ............... | A63B 21/055 |
| | | | | 482/51 |
| 2011/0275482 A1* | 11/2011 | Brodess | ............. | A63B 21/0428 |
| | | | | 482/8 |

FOREIGN PATENT DOCUMENTS

| | | |
|---|---|---|
| GB | 2 450 887 A | 1/2009 |
| GB | 2 482 269 A | 1/2012 |
| GB | 2 495 353 A | 4/2013 |
| JP | 2-241470 A | 9/1990 |
| KR | 10-0996592 B1 | 11/2010 |
| KR | 10-2013-0086912 A | 8/2013 |

\* cited by examiner

HORSE-RIDING TRAINING DEVICE

This application claims priority under 37 C.F.R. §119(a)-(d) to United Kingdom Patent Application No. 14 04597.5, filed Mar. 14, 2014, the disclosure of which is hereby incorporated by reference herein in its entirety.

BACKGROUND OF THE INVENTION

The present invention relates to a horse-riding training device. In particular, the present invention relates to self-powered horse-riding training device that provides a rider with an exercising effect similar to horse-riding.

Rocking-type exercising devices which provide an exercising effect similar to horse-back riding by rocking a saddle which the rider straddles have been well known for many years, and find application in fitness, medical and jockey rehabilitation environments. These earlier arrangements all have disadvantages. For example, conventional horse-riding exercising devices available on the market do not always offer a realistic riding position and style, and certainly do not provide the realism of a moving horse. The movements of conventional horse-riding exercising devices are often monotonous and simplistic and offer very little by way of feedback or stimulation to the rider. A rider who spends much time on conventional horse-riding exercising devices often succumbs to boredom as the exercise itself can be tedious.

Accordingly, there is a need for an improved horse-riding training device that readily and accurately mimics the riding feeling of a real horse. Furthermore, it is also desirable to have items of training equipment which are portable, quick and easy to set up. In addition, there is a need for connecting the horse-riding training device to an application software, typically for a portable electronic device, that provides instructional audio and/or audio-visual cues for the rider along with means for recording the rider's physical effort and efficiency. The present invention is designed with the foregoing in mind.

It is an object of the present invention to address one or more of the above problems and to provide an alternative and/or improved horse-riding training device.

BRIEF SUMMARY OF THE INVENTION

The present invention is as described herein and in the claims.

According to the present invention there is provided a horse-riding training device comprising: a base; a body portion for supporting a rider, the body portion being displaceably mounted on the base; a neck portion being pivotally connected to the base; and a resilient element which resists displacement of the body portion and the neck portion with respect to the base.

Preferably, the body portion is pivotally connected to the base.

Further preferably, the body portion and the neck portion are displaceable in a non-linear manner.

In use, the base may further comprise: at least one generally upwardly-projecting front frame member; at least one generally upwardly-projecting rear frame member; and at least one first cross-member.

Preferably, the upper end of the front frame member and the upper end of the rear frame member as connected to the first cross-member.

Further preferably, the at least one first cross-member is substantially horizontal.

In use, the front frame member and the rear frame member may be inclined at an angle of around 60° to around 70° to the horizontal.

Preferably, the body portion further comprises an outer shell which defines a realistic representation of a horse's back and flank in size and dimensions.

Further preferably, the outer shell is formed from fibreglass or similar durable material, and is secured to a plurality of generally elongate body support members.

In use, the body portion may further comprise: a first connecting bar, one end of which is pivotally connected to the front frame member, the other end of which is connected to the neck portion; a downwardly-projecting connecting rod, one end of which is pivotally connected to a pivot on the first connecting bar, the other end of which is pivotally connected to a supporting framework, the supporting framework having a plurality of generally elongate body support members secured thereto; and a second cross-member extending between the framework and a pivot on the first cross-member, the resilient element being disposed between the pivot on the first cross-member and the pivot on the first connecting bar.

Preferably, the neck portion further comprises: a second connecting bar, one end of which is secured to the first connecting bar, the other end of which is secured to a head section that is shaped and dimensioned to represent a horse's head; and an elongate support member, one end of which is secured to the head section, the other end of which is pivotally connected to the front frame member via a second pivot.

Preferably the elongate support member is pivotally connected to the head section.

In one embodiment, the elongate support member is rigid.

In another embodiment, the length of the elongate support member is variable. For example the elongate support member may comprise a telescopic elongate support member.

The elongate support member may comprise biasing means which urge the elongate support member towards a preferred configuration, e.g. to urge the elongate support member towards an extended configuration.

Further preferably, the neck portion further comprises a plurality of connectors, disposed on opposite sides of the head section, for attachment of a set of reins.

Further preferably, a strain gauge or pressure sensor is provided that measures the duration and pull on the reins.

In use, the horse-riding training device may further comprise a first positional sensor for detecting movement of the body portion and the neck portion with respect to the base.

Preferably, the first positional sensor is secured to any one of the front frame member, rear frame member or first cross-member, the input of first positional sensor being connected to the body portion or the neck portion via a mechanical linkage.

In use, the horse-riding training device may further comprise an additional member, one end of which can be removably attached or received within the first cross-member, the other end of which is connected to a whipping post that allows the rider to realistically simulate using a whip.

Preferably, a pair of elongate feet are positioned at each of the lower end of the front frame member and the lower end of the rear frame member.

Further preferably, one or more resilient or spring mechanisms are interposed between the feet and the lower end of the front frame member and the lower end of the rear frame member.

In use, a second positional sensor or accelerometer may be disposed on one or more of the front frame member, rear frame member or first cross-member to measure their lateral position and orientation.

Preferably, the output of the first positional sensor and/or second positional sensor and/or strain gauge is relayed to a portable electronic device over a wireless or wired connection.

Further preferably, the horse-riding training device wirelessly connects to the portable electronic device, e.g. using Bluetooth transmission protocol or Wi-Fi (IEEE 802.11) standard.

In use, the rider may use their bodyweight to compress the resilient element which pushes the neck portion both forwards and downwards away from the body portion.

Preferably, the resilient element is a tensile compressive spring.

Also according to the present invention there is provided a computer program product for use with a self-powered horse-riding training device as hereinbefore described, comprising: computer program means for receiving data indicative of rider physical effort and efficiency; computer program means for providing instructional audio and/or audio-visual cues for the rider; computer program means for combining the measured rider physical effort and efficiency and the rider response to the instructional audio and/or audio-visual cues and calculating one or more rider workout metrics; and computer program means for recording and displaying the one or more rider workout metrics.

Preferably, the computer program product may further comprise: computer program means for displaying a graphical representation of a horse-riding course and/or a virtual race to the rider.

Further preferably, the data indicative of rider physical effort and efficiency is selected from the group consisting, but not limited to, any one of the following: Pushes per Second, Average Push Length, Average Push Speed, Maximum Push Length, Maximum Push Speed, Time Pulling, Average Heart Rate, Peak Heart Rate, Heart Rate Zone, Heart Rate Recovery, Pushes Per Furlong and Total Pushes per Session.

In use, the computer program product may further comprise: computer program means for receiving the one or more rider workout metrics and graphically displaying one or more virtual opponents.

Preferably, the computer program means wirelessly transmits and receives data.

Further preferably, the computer program means wirelessly transmits and receives data, e.g. using a Bluetooth protocol or Wi-Fi (IEEE 802.11) standard.

In use, the computer program means may transmit and receive data over a wired connection.

It is believed that a horse-riding training device in accordance with the present invention at least addresses the problems outlined above. The advantages of the present invention are that an improved horse-riding training device is provided that readily and accurately mimics the riding feeling of a real horse. Advantageously, the horse-riding training device is portable, quick and easy to set up. Further advantageously, the horse-riding training device can be wirelessly connected to an application software, typically for a portable electronic device, that provides instructional audio and/or audio-visual cues for the rider along means for recording the rider's physical effort and efficiency.

It will be obvious to those skilled in the art that variations of the present invention are possible and it is intended that the present invention may be used other than as specifically described herein.

BRIEF DESCRIPTION OF THE DRAWINGS

Specific non-limiting embodiments of the invention will now be described by way of example only and with reference to the accompanying drawings, in which.

DETAILED DESCRIPTION

Figure 1:
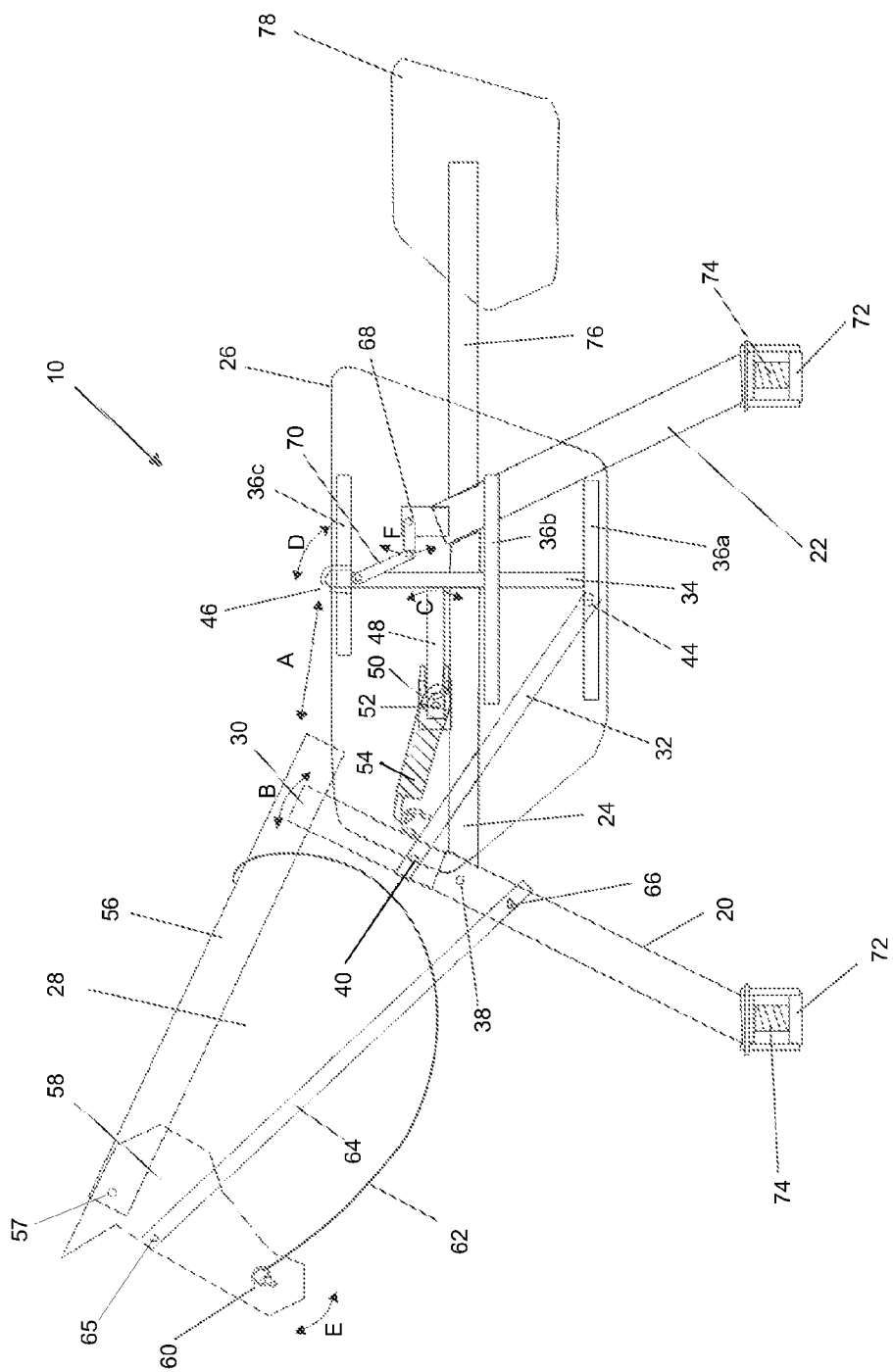
FIG. 1 is a cut-away side view of a first embodiment of horse-riding training device in accordance with the present invention.
Figure 2:
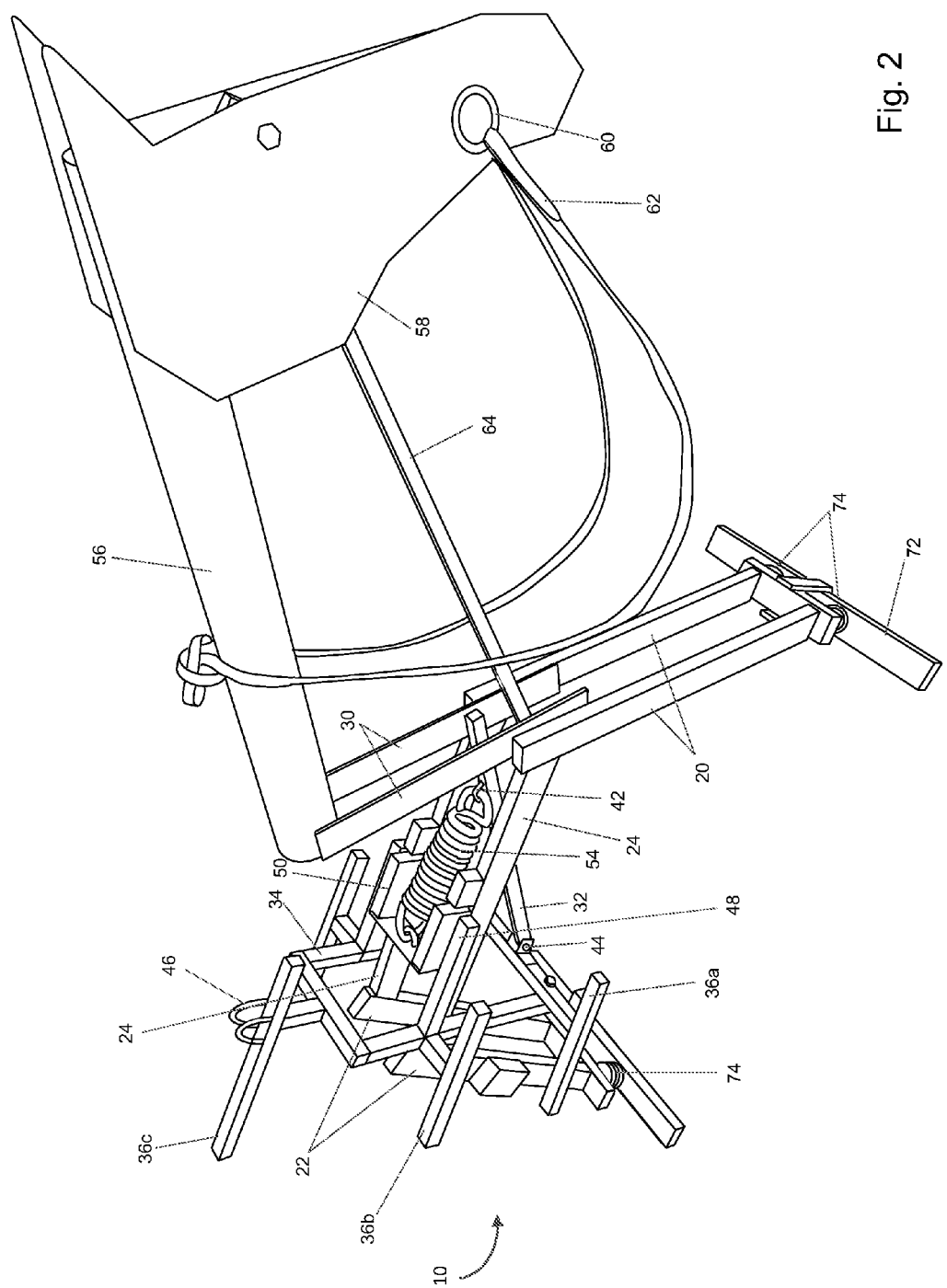
FIG. 2 is a front side perspective view of the horse-riding training device of FIG. 1.

Referring now to the drawings, a horse-riding training device 10 is shown in FIGS. 1 and 2. The horse-riding training device 10 comprises a supporting frame or base comprising two parallel generally upwardly-projecting and rearwardly inclined front frame members 20 and two parallel generally upwardly-projecting and forwardly inclined rear frame members 22. The upper ends of the front frame members 20 and the upper ends of the rear frame members 22 are interconnected by two parallel cross-members 24. The supporting frame or base supports the moving sections of the horse-riding training device 10 off the ground, and permits both upward and downwards movement, and fore and aft movement along the direction of a plane formed by the front frame members 20, rear frame members 22 and cross-members 24. As best illustrated in FIG. 1, the moving sections of the horse-riding training device 10 consist of two interconnected portions, namely a movable body portion 26 which is pivotally linked to a movable neck portion 28.

As indicated in FIG. 1, the movable body portion 26 defines a realistic representation of a horse's back and flank in size and dimensions so as to provide the most realistic simulation to the rider. The movable body portion 26 is formed from fibreglass or similar durable material and is secured to a number of generally elongate body support members 36a, 36b and 36c. The movable body portion, as generally depicted by numeral 26 in FIG. 1, is capable of receiving and bearing the weight of a rider and is able to move upwardly and downwardly, and along the direction of a plane formed by the front frame members 20, rear frame members 22 and cross-members 24, as described herein.

The movable body portion 26 is formed by two parallel first connecting bars 30. The lower ends of the first connecting bars 30 are pivotally connected at pivot 38 to the upwardly extending front frame members 20. When no rider is seated on the movable body portion 26, the first connecting bars extend upwardly and rearwardly at around the same angle as the front frame members 20, which is around 65°. The upper ends of the first connecting bars 30 are connected to a second connecting bar 56 which forms the part of the movable neck portion 28.

Approximately one-quarter along their length from the front frame members 20, the first connecting bars 30 are pivotally connected at a pivot 40 to an upper end of a generally downwardly-projecting connecting rod 32. The upper end of the generally downwardly-projecting connecting rod 32 also defines a U-bolt 42 around the pivot 40.

Figure 4:
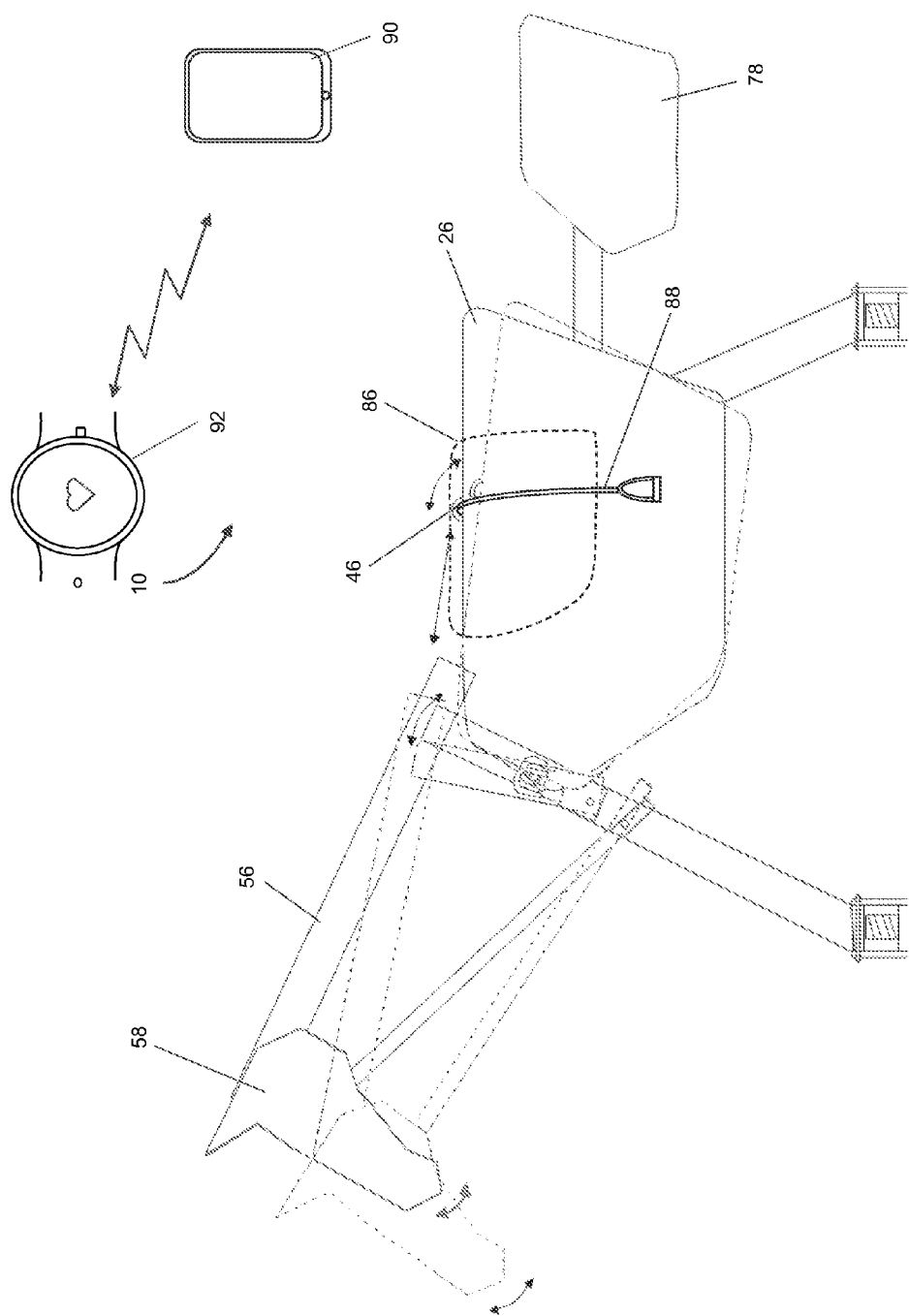
FIG. 4 is a side view of the horse-riding training device of FIG. 1 having a moulded outer shell secured thereon for riding, and shows that, in use, the horse-riding training device provides a realistic horse-riding motion.

The lower end of the connecting rod 32 is pivotally connected via pivot 44 to the bottom of a substantially vertical rectangular-shaped framework 34. The upper end of the substantially vertical rectangular-shaped framework 34 defines a U-shaped stirrup support 46 from which stirrups, as best shown in FIG. 4, can be attached. As illustrated in FIGS. 1 and 2, extending perpendicular to the framework 34 are a series of elongate parallel body support members 36a, 36b and 36c extending perpendicularly to the framework 34 which receive and support the movable body portion 26.

Two parallel cross-members 48 project forwardly at right angles from around the middle of each of the framework members 34, in a direction towards the movable neck portion 28. One end of each of the cross-members 48 is fixed to the framework 34 and the other end of each of the cross-members 48 is secured to the fixed cross-member 24 via a welded section 50 and a pivot 52. A tensile compressive spring 54 (i.e. an open spring which can be both compressed and extended) extends between the pivot 52 secured to the parallel cross-members 24, and an attachment loop 42 formed on the first connecting bar 30 slightly rearwardly of pivot 40.

The skilled person will appreciate that it is the compression and subsequent extension of the spring 54, which is achieved by the rider shifting their bodyweight generally fore and aft in a horse-riding simulating action and denoted by double-headed arrow A in FIG. 1, that extends and retracts the first connecting bar 30, through pivot 38, as denoted by double-headed arrow B in FIG. 1. This oscillatory action causes the framework 34, which is fixed to parallel cross-members 48, to rotate about pivot 52 in a motion depicted by double-headed arrow C. The movable body portion 26, which is secured to the body support members 36a, 36b and 36c, then raises and falls in a motion depicted by double-headed arrow D in FIG. 1. Therefore, the feeling and experience on the rider's body is akin to that experienced when riding a real horse.

As best illustrated in FIG. 1, the movement of the first connecting bar 30, as denoted by double-headed arrow B, also moves the second connecting bar 56 which forms the main structural support of the movable neck portion 28. The other end of the second connecting bar 56 is pivotally connected at pivot 57 to a head section 58 that is shaped and dimensioned to represent a horse's head. A loop connector 60 is positioned towards the bottom of the head section 58 and through which a set of reins 62 is secured. A rigid elongate support member 64 is pivotally secured at one end at pivot 65 to the head section 58, the other end of the support member being pivotally connected between the front frame members 20 via pivot 66. In this manner, movement of the first connecting bar 30, as denoted by double-headed arrow B in FIG. 1, causes a rising and falling motion of the head section 58 as indicated by double-headed arrow E. As can be appreciated by the skilled person, if the rider causes any tension in the reins 62 as head section 58 extends forwards and downwards this will serve to counter the effects of the rider shifting their bodyweight forwards and will cause the length of the push-out (i.e., the length the movable body portion 26 extends fore and aft) to be reduced. This again serves to reinforce that the riding feeling experienced by the rider of the device 10 is very similar to that of riding a real horse.

As best illustrated in FIG. 1, the movement of the movable body portion 26 relative to supporting frame or base can also be detected using a positional sensor 68, which can be any form of suitable transducer which takes a mechanical input and generates an electrical or digital output signal dependent on the input. The sensor 68 is connected to the movable body portion 26, via a mechanical linkage 70, and therefore detects the speed and length of the push-outs (i.e., each individual extension of the movable body portion 26 and their frequency), which is indicated generally by the reciprocating motion of the double-headed arrow F in FIG. 1.

The loop connector 60 also optionally includes a pressure sensor or strain gauge (not shown) that measures the duration and resistance of the pull on the reins 62. The skilled person will appreciate that data generated from this, and other sensors, can be transmitted wirelessly to a computer, smartphone or tablet 90, as indicated schematically in FIG. 4. In this way, useful metrics about the rider's workout can be recorded and displayed to the user or third parties.

Figure 3:
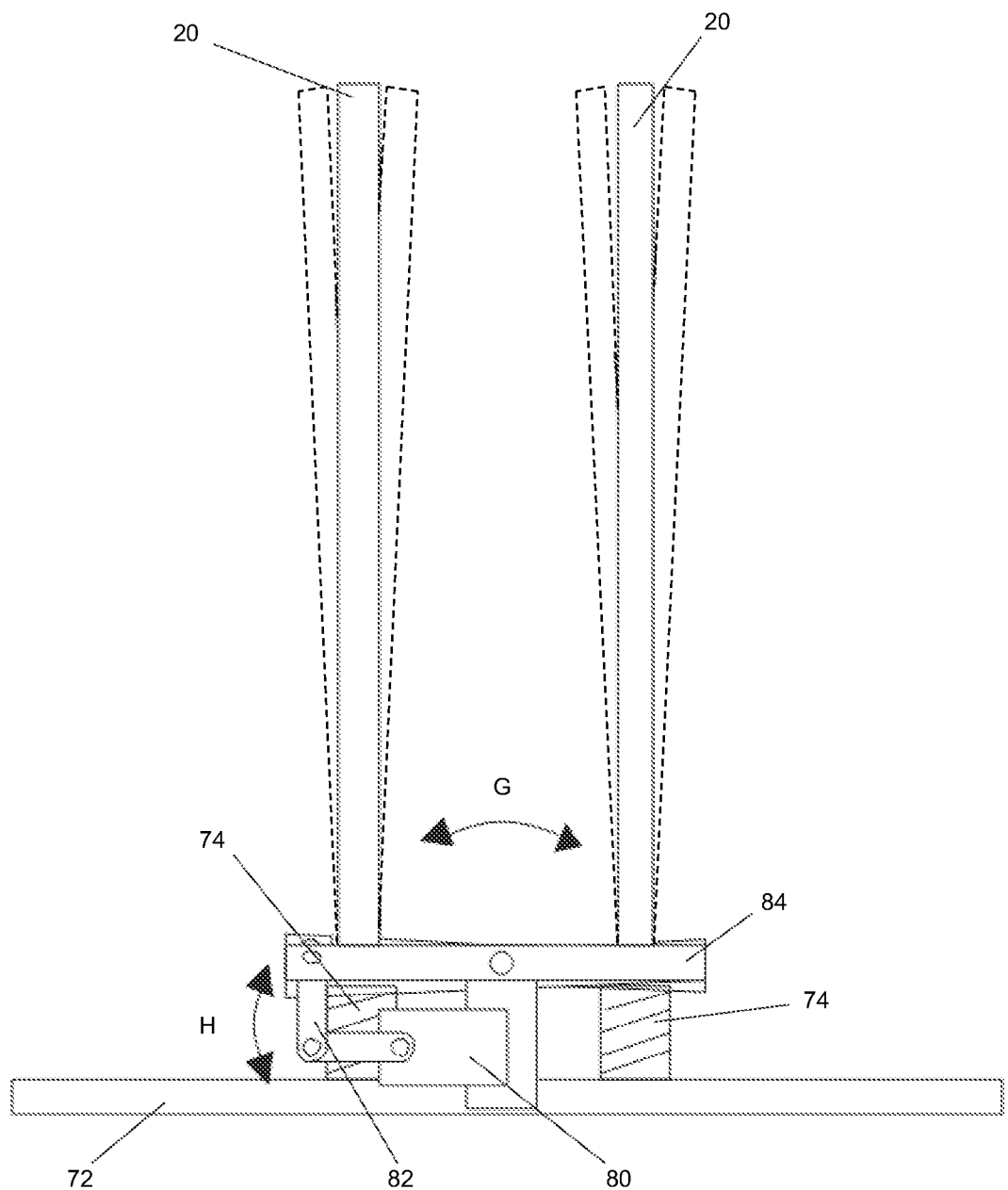
FIG. 3 is a front view of a frame which forms part of the horse-riding training device FIG. 1.

The horse-riding training device 10, as described above in FIGS. 1 and 2, is provided with suitable elongate feet 72 which are positioned at right angles to the lower ends of the front frame members 20 and the lower ends of the rear frame members 22. In an alternative embodiment of the invention, the horse-riding training device 10 can be supplied with one or more resilient or spring mechanisms 74 interposed between the feet 72 and the lower ends of the front frame members 20 and the lower ends of the rear frame members 22, as shown in FIG. 3. This therefore provides an additional aspect to the workout, i.e. the need for the rider to correctly balance laterally (i.e., perpendicular to the direction of a plane formed by the front frame members 20, rear frame members 22 and cross-members 24) on the horse-riding training device 10. It is also possible to include position sensors or accelerometers (not shown) on the front and rear frame members 20, 22, or the cross-members 26, to measure their position and orientation in use and provide active feedback.

In a further aspect of the invention, one end of an additional elongate frame member 76 is removably attached to the cross-member 24 and a whipping post 78 is connected to the opposite end, thereby allowing a rider to practice use of a whip.

FIG. 3 is a front view of the two parallel generally upwardly-projecting front frame members 20 (i.e. when viewed from the front of the horse-riding training device 10) which supports the horse-riding training device 10 of FIGS. 1 and 2. FIG. 3 shows detail of the one or more resilient or spring mechanisms 74 interposed between the feet 72 and the lower ends of the front frame members 20. The lateral movement of the front frame members 20 relative to feet 72 is detected by an accelerometer or positional sensor 80, which can be any form of suitable transducer that takes a mechanical input and generates an electrical or digital output signal dependent on the input. The sensor 80 is connected to the front frame members 20, which are mounted on a platform 84, via a mechanical linkage 82. As can be seen in FIG. 3, the representation of the front frame member 20 in dotted lines shows how the horse-riding training device 10 can move laterally. In use, the horse-riding training device 10 is allowed to deviate by ±10° from normal by selecting a suitable spring strength and positioning the springs 74 at least 100 mm apart. The skilled person will appreciate that data generated from this sensor 80, and other sensors, can be transmitted wirelessly to a computer, smartphone or tablet 90, as indicated schematically in FIG. 4.

FIG. 4 shows how the horse-riding training device 10 of the present invention can be used. As indicated in FIG. 4, the movable body portion 26 is formed from fibreglass or similar durable material and is secured to a number of generally elongate body support members (not shown in FIG. 4). The movable body portion 26 is capable of receiving and bearing the weight of a rider and is able to move both upward and downwards, and fore and aft along the direction of a plane formed by the supporting frame or base.

The movable body portion 26 provides a realistic representation of a horse in terms of size and dimensions. FIG. 4 also shows that, in use, the top of the movable body portion 26 defines a saddle 86 for the rider. In use, stirrups 88 are also connected to the U-shaped stirrup support 46. As can be seen with the representation of the horse-riding training device 10 shown in dotted lines, as the rider uses their bodyweight to effectively compress spring 54 (not shown in FIG. 4), the training device 10 effectively pushes-out the movable neck portion 28 away from the movable body portion 26. This exact same motion is exhibited when riding a real horse. Therefore, the riding effect that is achieved by the horse-riding training device 10 is incredibly realistic and allows a rider to develop and hone their riding fitness, style and technique.

FIG. 4 also shows schematically that the present invention can also be used with a wirelessly-connected computer, smartphone or tablet 90 which monitors the output of the sensors or accelerometers disposed on the horse-riding training device 10 and/or a heart rate monitor 92 worn by the rider. In a preferred embodiment, the horse-riding training device 10 wirelessly connects to computers, smartphones or tablets 90, or the like, using the Bluetooth protocol. The skilled person will appreciate that other wireless transmission protocols, such as, for example, Wi-Fi (IEEE 802.11 standard), would also be appropriate, or the computer, smartphone or tablet 90 could be connected to the horse-riding training device 10 via a wired connection.

The present invention also provides an application software, typically for a portable electronic device, that provides instructional audio and/or audio-visual cues for the rider along with a graphical representation of a horse-riding course for use with the horse-riding training device 10. The instructional cues alter as the intensity of the workout, or the route, changes or by a virtual sprint finish. In essence, the application software acts as personal trainer with full data recording and analysis tools.

The software of the present invention may be written in any one or more programming languages. In some embodiments, the software may be designed to operate on a computer system, having a central processing unit, memory and other typical computer components. As described herein, the computer system may include a computer, smartphone or tablet, or the like. In some embodiments, the software may reside on a server and operate on various remote computers. In some embodiments, the software may reside at least partially on a cloud-based system or on an internet-based system, where data, such as saved workouts, may be stored and exchanged with the software.

The application software of the present invention provides the following functionality:

Data Recording

For horse-riding training devices 10 that include positional sensors 68, the speed and length of the push-outs can be monitored. Sensors mounted on the loop connectors 60 can also measure duration and resistance on pulls to the reins. For horse-riding training devices 10 that include balance sensors 80, the balance while pulling/pushing out is monitored.

Therefore the application software records and displays data from the sensors in real-time, this includes, but not limited to:

Pushes per Second
    Average Push Length
    Average Push Speed
    Max Push Length
    Max Push Speed
    Time Pulling
    Average Heart Rate
    Peak Heart Rate
    Heart Rate Zone (Aerobic, Anaerobic, etc.)
    Heart Rate Recovery
    Pushes Per Furlong
    Total Pushes per Session Fitness Training The application software allows the user to set a workout of variable duration. Data displays can be customised to show real-time updates taken from the data set (as shown above). Data from workouts is recorded (full data set, not just what the user selected to view in real-time). Data from different sessions can be compared and overlaid graphically to visualise any improvements. Graphs can be displayed to show performance over time.

Virtual Race

User can elect to enact a virtual race in full 3D graphics (when the relevant hardware support is provided). The distance of the race is customisable. During the race, metrics are used to evaluate the rider's performance and set the speed of a digital "opponent" horse accordingly. Better performance translates to faster times. Full fitness data from the race is saved for later analysis and comparison. Different races can be compared and overlaid graphically to visualise any improvements. Graphs can be displayed to show performance over time. Users can opt to race against their previously saved times or a virtual partner who's performance is calculated on the current fitness/performance levels of the user. In either case, the race is run in real-time with a graphics representation of the opponent.

Fitness Evaluation

The application software runs a series of standardised instruction cues (a defined protocol) and captures data from the sensors and heart rate monitor. Various metrics are then utilised to evaluate the rider's performance. Heart rate recovery evaluation is performed after the exercise portion of the protocol. The rider's overall performance is evaluated and compared with data acquired from testing with professional jockeys. This evaluation is scored and stored alongside the comprehensive data (see above) captured during the session. Data from different sessions can be compared and overlaid graphically to visualise any improvements. Graphs can be displayed to show performance over time.

Data Analysis and Personal Training

Data from activities on the horse can be interchangeably overlaid and compared with each other. The application software also allows users to input extra data regarding activities unconnected to the horse. This enables the software to offer a more complete picture of physical activity/fitness training. Data that can be incorporated includes:

Weight—compatible with Bluetooth scales for automatic syncing of users weight, also allows manual input of users current weight; plots progress towards a stipulated target weight. Graphs show weight changes over time.

Other workouts—allows the user to enter workouts taken away from the horse (running, cycling etc.) and to record duration, calories burned, etc.

Activity tracking—keeps track of how often workouts are undertaken and compares with desired activity levels.

Diet/calories—allows the user to enter calories consumed and compare this to calories burned from fitness activities.

Figure 5:
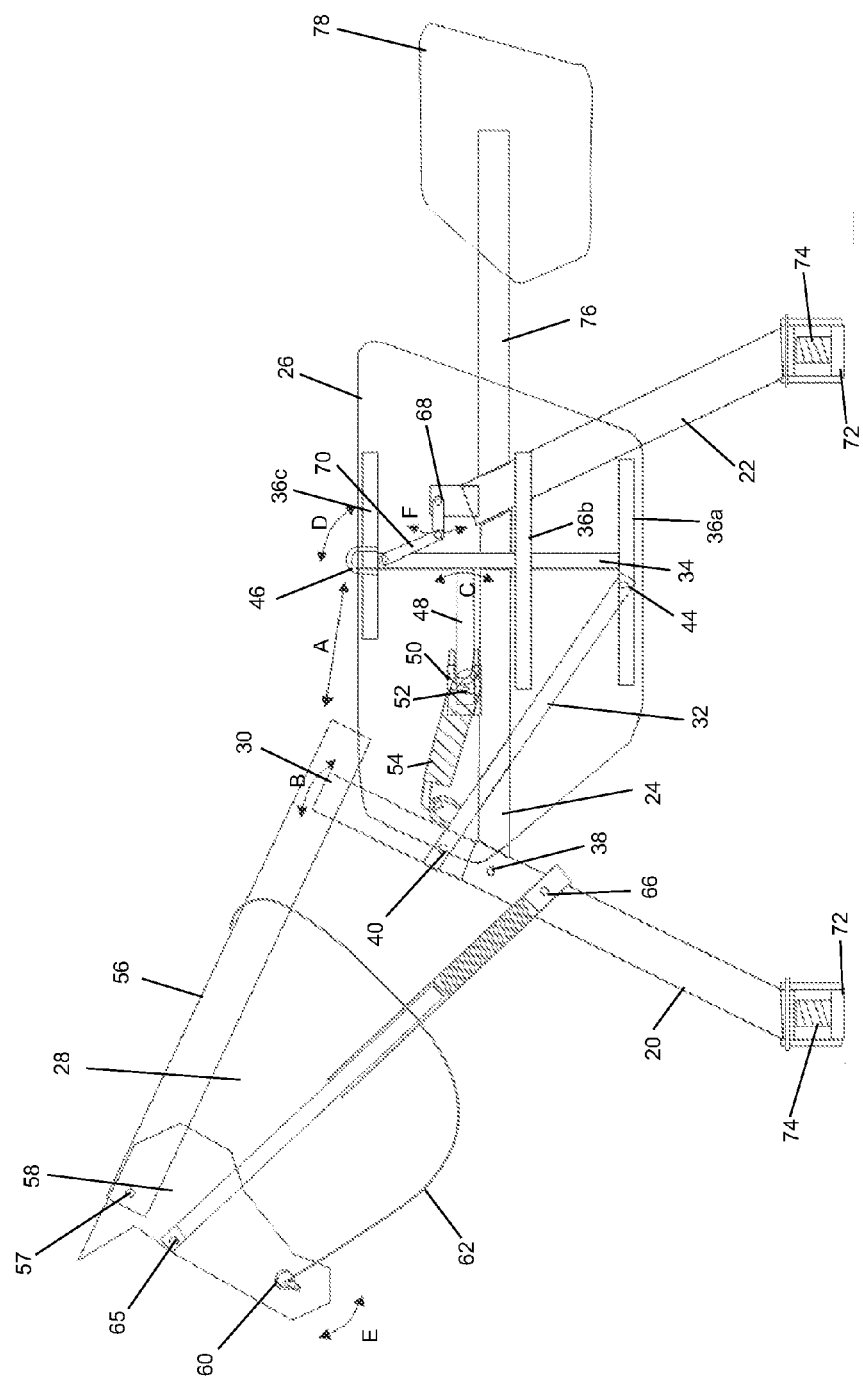
FIG. 5 is a cut-away side view of a second embodiment of horse-riding training device in accordance with the present invention.

A second embodiment of the invention is illustrated in FIG. 5. The second embodiment is very similar to the first embodiment and the same reference numerals as for the first embodiment have been used to identify the same features.

The only difference from the first embodiment is the replacement of the rigid elongate support member 64 with telescopic elongate support member 164 of variable length. In particular, the support member 164 comprises a tubular lower portion 166 which is pivotally connected between the front support members 20 at pivot 66, and a cylindrical upper portion 168 whose lower end is slidably received in the tubular lower portion 166 and whose upper end is pivotally connected at pivot 65 to the head section 58. The tubular lower portion 166 also houses a compression spring 170 which is engaged with, and compressed by, the cylindrical upper portion 168 as the upper portion slides into the tubular lower portion 166.

With the second embodiment, pulling rearwardly on the reins 62 causes the head section 58 to pivot downwardly about pivot 57, which causes the cylindrical upper portion 168 of the telescopic support member 164 to slide into the tubular lower portion 166. This causes the spring 170 within the tubular lower portion to compress as long as the reins continue to be pulled with sufficient force. Releasing or reducing the pulling force on the reins allows the spring to displace the cylindrical upper portion 168 of the telescopic support member in the opposite direction, which in turn causes the head section to pivot upwardly.

The use of a compressible support member 164 allows the reins to have a "soft" feel when pulled. The reins are typically pulled during the first part of a race when the jockey is trying to prevent the horse from running too fast in order to save energy for the end of the race.

Other than the above modification, the construction and operation of the second embodiment are identical to the construction and operation of the first embodiment.

Various alterations and modifications may be made to the present invention without departing from the scope of the invention.

What is claimed is:

1. A horse-riding training device comprising:
   a base having a front end and a rear end, and comprising:
      at least one generally upwardly-projecting front frame member,
      at least one generally upwardly-projecting rear frame member, and
      at least one first cross-member;
   a body portion for supporting a rider, the body portion being displaceably mounted on the base, the body portion comprising:
      a first connecting bar, a first end of which is pivotally connected to the front frame member, and a second end of which is connected to the neck portion,
      a downwardly-projecting connecting rod, a first end of which is pivotally connected to a first pivot on the first connecting bar, and a second end of which is pivotally connected to a supporting framework, the supporting framework having a plurality of generally elongate body support members secured thereto, and
      a second cross-member extending between the supporting framework and a second pivot on the first cross-member;
   a neck portion pivotally connected to the base and extending outwardly from the base in a forward direction; and
   a resilient element that is configured to resist displacement of the body portion and the neck portion with respect to the base, the resilient element being disposed between the second pivot on the first cross-member and the first pivot on the first connecting bar.

2. The horse-riding training device of claim 1, wherein the body portion is pivotally connected to the base.

3. The horse-riding training device of claim 1, wherein the body portion and the neck portion are displaceable in a non-linear manner.

4. The horse-riding training device of claim 1, wherein an upper end of the front frame member and an upper end of the rear frame member are connected to the first cross-member.

5. The horse-riding training device of claim 1, wherein the at least one first cross-member is substantially horizontal.

6. The horse-riding training device of claim 1, wherein the front frame member and the rear frame member are inclined at an angle of around 60° to around 70° to the horizontal.

7. The horse-riding training device of claim 1, wherein the body portion further comprises an outer shell which defines a realistic representation of a horse's back and flank in size and dimensions.

8. The horse-riding training device of claim 7, wherein the outer shell is formed from a durable material, and is secured to a plurality of generally elongate body support members.

9. The horse-riding training device of claim 1, wherein the neck portion further comprises:
   a second connecting bar, a first end of which is secured to the first connecting bar, and a second end of which is secured to a head section that is shaped and dimensioned to represent a horse's head; and
   an elongate support member, a first end of which is secured to the head section, and a second end of which is pivotally connected to the front frame member via a third pivot.

10. The horse-riding training device of claim 9, wherein the elongate support member is pivotally connected to the head section.

11. The horse-riding training device of claim 9, wherein the elongate support member is rigid.

12. The horse-riding training device of claim 9, wherein a length of the elongate support member is variable.

13. The horse-riding training device of claim 12, comprising a telescopic elongate support member.

14. The horse-riding training device of claim 12, comprising biasing means that are configured to urge the elongate support member towards a preferred configuration.

15. The horse-riding training device of claim 14, wherein the biasing means are configured to urge the elongate support member towards an extended configuration.

16. The horse-riding training device of claim 9, wherein the neck portion further comprises a plurality of connectors, disposed on opposite sides of the head section, for attachment of a set of reins.

17. The horse-riding training device of claim 16, further comprising at least one of a strain gauge or pressure sensor that is configured to measure a duration and pull on the reins.

18. The horse-riding training device of claim 1, further comprising a first positional sensor that is configured to detect movement of the body portion and the neck portion with respect to the base.

19. The horse-riding training device of claim 18, wherein the first positional sensor is secured to the base, an input of first positional sensor being connected to one of the body portion or the neck portion via a mechanical linkage.

20. A horse-riding training device comprising:
a base having a front end and a rear end, and comprising:
at least one generally upwardly-projecting front frame member,
at least one generally upwardly-projecting rear frame member, and
at least one first cross-member;
a body portion for supporting a rider, the body portion being displaceably mounted on the base;
a neck portion pivotally connected to the base and extending outwardly from the base in a forward direction;
a resilient element that is configured to resist displacement of the body portion and the neck portion with respect to the base; and
an additional member, a first end of which is one of removably attached or received within the first cross-member, and a second end of which is connected to a whipping post that is configured to allow a rider to simulate using a whip.

21. A horse-riding training device comprising:
a base having a front end and a rear end, and comprising:
at least one generally upwardly-projecting front frame member,
at least one generally upwardly-projecting rear frame member, and
at least one first cross-member;
a body portion for supporting a rider, the body portion being displaceably mounted on the base;
a neck portion pivotally connected to the base and extending outwardly from the base in a forward direction;
a resilient element that is configured to resist displacement of the body portion and the neck portion with respect to the base;
a pair of elongate feet positioned at each of a lower end of the front frame member and a lower end of the rear frame member; and
one or more resilient or spring mechanisms interposed between the feet and the lower end of the front frame member and the lower end of the rear frame member.

22. A horse-riding training device comprising:
a base having a front end and a rear end;
a body portion for supporting a rider, the body portion being displaceably mounted on the base;
a neck portion pivotally connected to the base and extending outwardly from the base in a forward direction;
a resilient element that is configured to resist displacement of the body portion and the neck portion with respect to the base;
a first positional sensor that is mounted on the base and is configured to detect movement of the body portion and the neck portion with respect to the base; and
at least one of a second positional sensor and an accelerometer disposed on the base to measure a lateral position and orientation.

23. The horse-riding training device of claim 22 wherein an output of at least one of the first positional sensor and the second positional sensor is relayed to a portable electronic device over a wired or wireless connection.

24. The horse-riding training device of claim 23, wherein the horse-riding training device wirelessly connects to the portable electronic device.

25. The horse-riding training device of claim 1, wherein the resilient element is compressed by bodyweight of the rider to push the neck portion both forwards and downwards away from the body portion.

26. The horse-riding training device of claim 1, wherein the resilient element is a tensile compressive spring.

27. A horse-riding training device comprising:
a base having a front end and a rear end;
a body portion for supporting a rider, the body portion being displaceably mounted on the base;
an elongate neck portion pivotally connected to the base at a first end of the neck portion and extending outwardly from the base in a forward direction;
a resilient element that is configured to resist displacement of the body portion and the neck portion with respect to the base;
a head portion pivotally connected to a second end of the neck portion opposite the first end of the neck portion; and
an elongate support member pivotally connected at a first end to the head portion and pivotally connected at a second end, opposite the first end, to the base.

* * * * *